US012508397B2

(12) United States Patent
Burkholz et al.

(10) Patent No.: US 12,508,397 B2
(45) Date of Patent: Dec. 30, 2025

(54) TUBULAR INSTRUMENT AND RELATED DEVICES AND METHODS

(71) Applicant: Becton, Dickinson and Company, Franklin Lakes, NJ (US)

(72) Inventors: Jonathan Karl Burkholz, Salt Lake City, UT (US); Megan Scherich, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 316 days.

(21) Appl. No.: 17/143,095

(22) Filed: Jan. 6, 2021

(65) Prior Publication Data

US 2021/0220605 A1 Jul. 22, 2021

Related U.S. Application Data

(60) Provisional application No. 62/963,929, filed on Jan. 21, 2020.

(51) Int. Cl.
*A61M 25/00* (2006.01)

(52) U.S. Cl.
CPC .... *A61M 25/0043* (2013.01); *A61M 25/0074* (2013.01); *A61M 2205/02* (2013.01)

(58) Field of Classification Search
CPC .............. A61M 25/0053; A61M 25/09; A61M 25/005; A61M 25/0052; A61M 25/0054; A61M 25/0068; A61M 25/0105; A61M 25/0133; A61M 25/0144; A61M 25/0147;
(Continued)

(56) References Cited

U.S. PATENT DOCUMENTS 2,211,975 A * 8/1940 Hendrickson ....... A61M 25/005 138/133
3,416,531 A * 12/1968 Miles .............. A61M 25/09041 604/95.04
(Continued)

FOREIGN PATENT DOCUMENTS

DE 102006007974 A1 * 8/2007 ........ A61M 25/0053
EP 2351641 A1 8/2011
(Continued)

OTHER PUBLICATIONS

Hardness Conversion Chart of Plastics, https://plastics.ulprospector.com/properties/hardness-conversion-chart (accessed Apr. 3, 2023) (Year: 2023).*
(Continued)

*Primary Examiner* — Bhisma Mehta
*Assistant Examiner* — Adam J. Cermak
(74) *Attorney, Agent, or Firm* — The Webb Law Firm

(57) ABSTRACT

A delivery device to deliver a tubular instrument into a catheter. The delivery device may include the tubular instrument, which may include an annular wall. The annular wall may include a distal end and may form a lumen. The annular wall may include a first annular section and a second annular section proximal to the first annular section. A durometer of the second annular section may be greater than a durometer of the first annular section. The tubular instrument may include a distal opening within the distal end of the annular wall. The first annular section may include the distal opening.

14 Claims, 10 Drawing Sheets

(58) Field of Classification Search
CPC ........... A61M 2025/0059; A61M 2025/09083; A61M 2025/09133; A61M 2025/09175
See application file for complete search history.

(56) References Cited

U.S. PATENT DOCUMENTS 3,757,768 A * 9/1973 Kline ................ A61M 25/0662 604/95.01
4,342,313 A 8/1982 Chittenden
4,430,083 A * 2/1984 Ganz ...................... A61B 6/504 604/529
4,737,153 A * 4/1988 Shimamura ....... A61M 16/0425 138/131
4,739,768 A * 4/1988 Engelson .............. A61M 25/09 604/528
5,057,092 A * 10/1991 Webster, Jr. ........ A61M 25/005 138/123
5,102,401 A * 4/1992 Lambert ............. A61L 33/0011 604/264
5,176,660 A * 1/1993 Truckai ............... A61M 25/005 138/123
5,226,899 A * 7/1993 Lee ......................... B29C 48/21 604/524
5,244,619 A * 9/1993 Burnham ............ A61M 25/005 264/171.2
5,348,536 A 9/1994 Young et al.
5,374,245 A * 12/1994 Mahurkar ........... A61M 25/005 604/43
5,453,099 A * 9/1995 Lee ....................... A61L 29/085 604/524
5,569,220 A * 10/1996 Webster, Jr. ...... A61M 25/0045 600/374
5,713,860 A * 2/1998 Kaplan ............... A61M 25/104 604/103.01
5,782,740 A * 7/1998 Schneiderman .... A61M 25/104 604/524
5,792,124 A * 8/1998 Horrigan ............. A61M 25/005 604/525
5,840,008 A * 11/1998 Klein ................... A61N 5/1002 600/7
5,911,715 A * 6/1999 Berg ..................... F16L 11/081 604/525
6,165,163 A * 12/2000 Chien ............... A61M 25/0053 604/524
6,210,395 B1 * 4/2001 Fleischhacker ....... A61M 25/09 604/524
6,450,948 B1 * 9/2002 Matsuura ............. A61B 1/0055 606/1
6,569,150 B2 * 5/2003 Teague ................ A61M 27/008 604/524
6,579,221 B1 * 6/2003 Peterson .............. A61N 5/1002 600/3
6,709,429 B1 * 3/2004 Schaefer .................. D04C 1/06 604/524
7,351,238 B2 * 4/2008 Lee ................... A61M 25/0029 604/525
7,771,369 B2 * 8/2010 Griffin .................. A61M 25/01 604/528
8,377,035 B2 * 2/2013 Zhou ................. A61M 25/0043 604/524
8,591,495 B2 * 11/2013 Fischell ............ A61M 25/0012 604/526
9,622,892 B2 * 4/2017 Baker ............... A61M 25/0045
9,623,206 B2 * 4/2017 Melsheimer .......... A61M 25/01
9,717,559 B2 * 8/2017 Ditter ................... A61B 5/0538
10,076,272 B2 * 9/2018 Devgon ............. A61B 5/15003
10,238,325 B2 * 3/2019 Burkholz ......... A61B 5/150343
10,668,258 B1 * 6/2020 Calhoun ............... A61M 29/02
11,090,461 B2 * 8/2021 Ehrenreich ...... A61B 5/150641
11,090,465 B2 * 8/2021 Weber ................. A61M 25/005
11,173,279 B2 * 11/2021 Wada ................ A61M 25/0053
2001/0034514 A1 * 10/2001 Parker ................. A61M 25/005 604/525
2003/0065352 A1 * 4/2003 Yang ................... A61M 25/008 604/103.1
2006/0089618 A1 4/2006 McFerran et al.
2006/0111649 A1 * 5/2006 Zhou ................. A61M 25/0053 600/585
2006/0270977 A1 * 11/2006 Fisher ................... A61M 29/02 604/103.04
2007/0016133 A1 * 1/2007 Pepper .............. A61M 25/0052 604/103.04
2007/0100285 A1 * 5/2007 Griffin .............. A61M 25/0013 604/164.11
2009/0163891 A1 * 6/2009 Ewing ............... A61M 25/1034 604/526
2010/0049168 A1 * 2/2010 Parker ................. A61M 25/005 604/527
2012/0053415 A1 * 3/2012 Bunch ............... A61M 25/0136 600/121
2012/0277627 A1 * 11/2012 Devgon ........... A61B 5/150717 600/576
2012/0277630 A1 11/2012 Devgon
2013/0289697 A1 * 10/2013 Baker ............... A61M 25/0053 156/244.11
2014/0171919 A1 6/2014 Blacker
2014/0214006 A1 * 7/2014 Hiroshige ......... A61M 25/0012 604/527
2015/0173782 A1 6/2015 Garrison et al.
2016/0331897 A1 * 11/2016 Anand ................ A61M 5/1723
2018/0272107 A1 * 9/2018 Ehrenreich ...... A61B 5/150748
2018/0296731 A1 * 10/2018 Lim ................... C08G 18/6674
2019/0021640 A1 1/2019 Burkholz et al.
2019/0224456 A1 * 7/2019 Kon ...................... A61M 25/09
2019/0321590 A1 10/2019 Burkholz et al.
2019/0321595 A1 10/2019 Spataro et al.
2019/0351194 A1 * 11/2019 Korkuch ............... A61M 39/02
2020/0016374 A1 1/2020 Burkholz et al.
2020/0054861 A1 * 2/2020 Korkuch ............. A61M 60/865
2020/0061340 A1 * 2/2020 Mixter ................... A61B 8/445
2020/0069927 A1 * 3/2020 Malek ............... A61M 25/0053
2020/0170559 A1 6/2020 Burkholz et al.
2020/0305733 A1 * 10/2020 Caron .................. A61B 5/6851
2020/0316313 A1 * 10/2020 Ishida ................. A61M 5/3293
2021/0023339 A1 * 1/2021 Hayes ................ A61B 1/00078
2021/0154402 A1 * 5/2021 Close ............... A61B 5/150221
2023/0372671 A1 * 11/2023 Devgon ............. A61M 25/0113

FOREIGN PATENT DOCUMENTS

EP 3395393 A1 * 10/2018 ............ A61M 25/09
EP 3398625 A1 * 11/2018 ............. A61L 29/02
EP 2635339 B1 * 1/2019 ........ A61M 25/0012
JP 2005503898 A * 2/2005 ............ A61M 29/02
JP 2014516643 A 7/2014
JP 2017202042 A 11/2017
WO WO-9117782 A1 * 11/1991 ........ A61M 25/0032
WO WO-9207594 A1 * 5/1992 ............ A61M 25/09
WO WO-2006127929 A2 * 11/2006 ........ A61M 25/0032
WO 2007136981 A1 11/2007
WO WO-2010060889 A1 * 6/2010 ........ A61M 25/0045
WO WO-2016033143 A1 * 3/2016 ......... A61B 5/15003
WO WO-2016049149 A2 * 3/2016 ......... A61B 17/3415
WO WO-2017151052 A1 * 9/2017
WO WO-2019124422 A1 * 6/2019 .............. A61M 1/16

OTHER PUBLICATIONS

Overview of materials for Polytetrafluoroethylene (PTFE), Extruded, MatWeb, https://www.matweb.com/search/DataSheet.aspx?MatGUID=4e0b2e88eeba4aaeb18e8820f1444cdb (accessed Mar. 30, 2023) (Year: 2023).*
Hardness and Microstructure of Binary and Ternary Nitinol Compounds, Stanford, M.K., NASA/TM—2016-218946/REV1, Dec. 2019 (Year: 2019).*
MatWeb Arkema Pebax® 3533 SA 01 TPA material data sheet, https://www.matweb.com/search/DataSheet.aspx?MatGUID=b93d4541f4084ae9bcc0e0f789e2cabd (accessed Apr. 6, 2023) (Year: 2023).*

(56) References Cited

OTHER PUBLICATIONS

Hardness Conversion Chart, Carbide Depot, www.carbidedepot.com/formulas-hardness.htm (accessed Apr. 6, 2023) (Year: 2023).*

* cited by examiner

TUBULAR INSTRUMENT AND RELATED DEVICES AND METHODS

RELATED APPLICATIONS

This application claims the benefit of U.S. Provisional Application No. 62/963,929, filed Jan. 21, 2020, and entitled TUBULAR INSTRUMENT AND RELATED DEVICES AND METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter is often used for acquiring a blood sample at a time of catheter placement, but the catheter is less frequently used for acquiring a blood sample during the catheter dwell period. Therefore, when a blood sample is required, an additional needle stick is often needed to provide vein access for blood collection, which may be painful for the patient and result in higher material costs.

In some instances, in order to avoid the additional needle stick, a tubular instrument may be used to access the vasculature of the patient via the catheter. The tubular instrument may be inserted through the catheter and into the vasculature to extend a life of the catheter and allow blood withdrawal through the catheter without the additional needle stick. Generally the tubular instrument has a high stiffness and a thin wall. The high stiffness allows advancement of the tubular instrument without buckling, and the thin wall facilitates increased flow rates through the tubular instrument. However, the high stiffness in combination with the thin wall results in a sharp, stiff distal edge of the tubular instrument, which can induce trauma to the vein wall. In particular, as the tubular instrument is advanced distally beyond a distal tip of the catheter, the tubular instrument may damage a vein wall and increase a risk of thrombus and other complications.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices. In particular, the present disclosure relates to a tubular instrument and related devices and methods. In some embodiments, a delivery device to deliver a tubular instrument into a catheter may facilitate an increased dwell period of the catheter. In further detail, the delivery device may be used to advance the tubular instrument into the catheter and/or beyond a distal tip of the catheter for fluid infusion or blood draw when the catheter is compromised or nearing an end of its life.

In some embodiments, the delivery device may include the tubular instrument, which may include axial structural stiffness to facilitate advancement of the tubular instrument without buckling. In some embodiments, the tubular instrument may also have an inner diameter to facilitate high flow rates for fluid infusion and/or blood draw. While providing axial structural stiffness and high flow rates, unlike tubular instruments in the prior art, the tubular instrument may also provide gentle, soft contact between the tubular instrument and a vein wall, which may reduce trauma to the vein wall. In some embodiments, the tubular instrument may also sustain flexural bending. In some embodiments, advantages of the tubular instrument may result from a multi-material structure.

In some embodiments, the tubular instrument may include an annular wall. In some embodiments, the annular wall may include a distal end and a proximal end. In some embodiments, the annular wall may form a lumen, which may extend through the distal end of the annular wall and/or the proximal end of the annular wall. In some embodiments, the tubular instrument may include a distal opening, which may be disposed within the distal end of the annular wall.

In some embodiments, the tubular instrument may include one or more stripes, which may be disposed within the annular wall. In some embodiments, the stripes may extend proximally from the distal end of the annular wall. In some embodiments, the stripes may be aligned with a longitudinal axis of the tubular instrument. In some embodiments, the stripes may extend proximally from the distal opening. In some embodiments, the stripes may extend proximally from a position proximal to the distal opening.

In some embodiments, an outer perimeter of each of the stripes may be surrounded by the annular wall. In some embodiments, the stripes may be co-extruded within the annular wall. In some embodiments, the stripes may be constructed of a first material, and the annular wall may be constructed of a second material. In some embodiments, the first material may have a greater durometer than the second material. Thus, in some embodiments, the stripes may be stiffer than the annular wall.

In some embodiments, the first material may include thermoplastic elastomer, thermoplastic polyurethane, polyurethane, nylon, polyimide, silicon, or another suitable polymer. In some embodiments, the first material may include metal. In some embodiments, each of the stripes may include a wire, which may be constructed of metal. In some embodiments, the wire may be configured to hold the tubular instrument in a curved position in response to the wire being bent. In some embodiments, the second material may include polypropylene, polyurethane, polyurethane, nylon, polyimide, silicon, or another suitable polymer. In some embodiments, the second material may be similar to the first material but lower density.

In some embodiments, the stripes may provide stiffness to the tubular instrument, which may facilitate advancement of the tubular instrument through a catheter assembly and beyond the distal tip of the catheter without buckling. In some embodiments, the second material may be disposed on the outer surface of the tubular instrument, which may provide a softer contact surface with the vein.

In some embodiments, the annular wall may include an inner surface and an outer surface. In some embodiments, the inner surface may be proximate the lumen of the tubular instrument. In some embodiments, the inner surface may be cylindrical and/or the stripes may protrude to form ribs on the outer surface. In some embodiments, other than the ribs on the outer surface formed by the stripes, the outer surface may be cylindrical. In some embodiments, the outer surface may be cylindrical and/or the stripes may protrude to form ribs on the inner surface. In some embodiments, other than the ribs on the other surface formed by the stripes, the outer surface may be cylindrical. In some embodiments, other than the ribs on the inner surface formed by the stripes, the inner surface may be cylindrical.

In some embodiments, the stripes may be closer to the inner surface than the outer surface. In some embodiments, the stripes may be closer to the outer surface than the inner surface. In some embodiments, the stripes may be spaced around the annular wall. In some embodiments, the stripes may be evenly spaced around the annular wall.

In some embodiments, the annular wall may include a first annular section and a second annular section distal to the first annular section. In some embodiments, a durometer of the first annular section may be greater than a durometer of the second annular section. In some embodiments, the second annular section may include the distal opening.

In some embodiments, the first annular section may be constructed of the first material. In some embodiments, the second annular section may be constructed of the second material. In some embodiments, a durometer of the first material may be greater than a durometer of the second material. In some embodiments, a thickness of the first annular section may be greater than a thickness of the second annular section. In some embodiments, an outer surface of the second annular section may include multiple grooves, which may extend perpendicular to a longitudinal axis of the tubular instrument.

In some embodiments, the first annular section may include one or more stripes, which may be co-extruded within the first annular section. In some embodiments, the stripes may be aligned with the longitudinal axis of the tubular instrument. In some embodiments, the stripes may be constructed of the first material. In some embodiments, the second annular section may be constructed of the second material. In some embodiments, the first material may have a greater durometer than the second material.

In some embodiments, the annular wall may include a third annular section between the first annular section and the second annular section. In some embodiments, the third annular section may be proximate the first annular section and/or the second annular section. In some embodiments, the first annular section may be proximate the second annular section.

In some embodiments, the distal end of the annular wall may include a first annular layer and a second annular layer. In some embodiments, the first annular layer may be disposed within the second annular layer. In some embodiments, the second annular layer may surround the first annular layer. In some embodiments, the first annular layer may be constructed of the first material. In some embodiments, the second annular layer may be constructed of the second material. In some embodiments, the first material may have a greater durometer than the second material.

In some embodiments, the distal end of the annular wall may include a third annular layer, which may be disposed within the first annular layer and the second annular layer. In some embodiments, the first annular layer may surround the third annular layer. In some embodiments, the third annular layer may be constructed of the second material or a third material. In some embodiments, the first material may have a greater durometer than the third material.

In some embodiments, a thickness of the second annular layer may be greater than a thickness of the first annular layer at a first position along a length of the tubular instrument. In some embodiments, the thickness of the second annular layer may be a same thickness as the thickness of the first annular layer at a second position along the length of the tubular instrument. In some embodiments, the second position may be proximal to the first position. In some embodiments, the thickness of the second annular layer may be less than the thickness of the first annular layer at a third position along the length of the tubular instrument. In some embodiments, the third position may be proximal to the second position.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
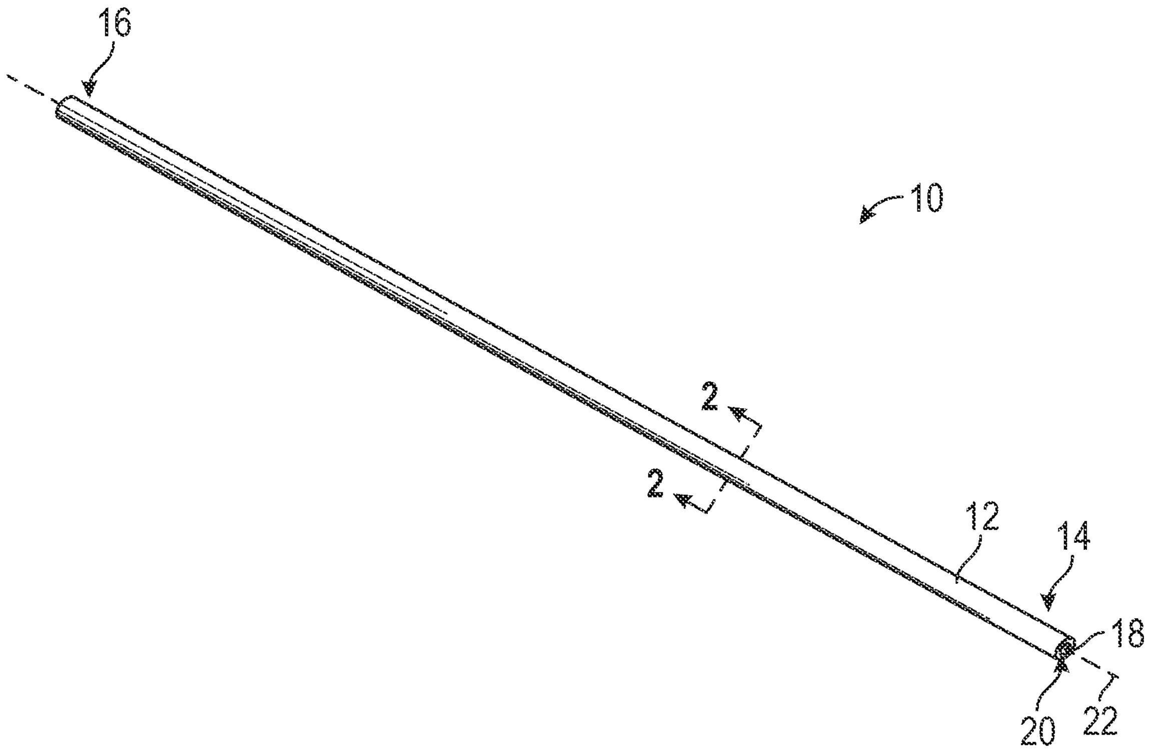
FIG. 1 is an upper perspective view of an example tubular instrument, according to some embodiments.

Referring now to FIG. 1, in some embodiments, a delivery device to deliver a tubular instrument 10 into a catheter may facilitate an increased dwell period of the catheter. In further detail, the delivery device may be used to advance the tubular instrument 10 into the catheter and/or beyond a distal tip of the catheter for fluid infusion or blood draw when the catheter is compromised or nearing an end of its life. In some embodiments, the tubular instrument 10 may include axial structural stiffness to facilitate advancement of the tubular instrument 10 without buckling. In some embodiments, the tubular instrument 10 may also have an inner diameter to facilitate high flow rates for fluid infusion and/or blood draw. While providing axial structural stiffness and high flow rates, unlike the tubular instrument of the prior art, the tubular instrument 10 may also provide gentle, soft contact between the tubular instrument 10 and a vein wall, which may reduce trauma to the vein wall. In some embodiments, the tubular instrument 10 may also sustain flexural bending.

In some embodiments, the tubular instrument 10 may include an annular wall 12. In some embodiments, the annular wall 12 may include a distal end 14 and a proximal end 16. In some embodiments, the annular wall 12 may form a lumen 18, which may extend through the distal end 14 of the annular wall 12 and/or the proximal end 16 of the annular wall 12. In some embodiments, the tubular instrument 10 may include a distal opening 20, which may be disposed within the distal end 14 of the annular wall 12.

In some embodiments, the distal opening 20 may be aligned with a longitudinal axis 22 of the tubular instrument 10. In other embodiments, a portion of the distal end 14 aligned with the longitudinal axis 22 may be closed, and the distal opening 20 may be disposed lateral to the longitudinal axis 22 through the annular wall 12. In some embodiments, the distal end 14 may include one or more diffusion holes (not illustrated), which may extend through the annular wall 12. In some embodiments, the diffusion holes may be disposed proximal to the distal opening 20. In some embodiments, the distal end 14 may be blunt, tapered, or another suitable shape.

Referring now to FIG. 2A-2F, in some embodiments, the tubular instrument 10 may include one or more stripes 24, which may be disposed within the annular wall 12. In some embodiments, the stripes 24 may include long narrow bands or strips. In some embodiments, each of the stripes 24 may have a uniform or variable diameter along a length of the stripe 24. In some embodiments, the stripes 24 may allow the annular wall 12 to be thin for a high flow rate through the tubular instrument 10, without increasing a sharpness of the distal end 14 and a risk of trauma to the vein.

In some embodiments, the stripes 24 may extend along all or a portion of a length of the annular wall 12 between the distal end 14 and the proximal end 16. In some embodiments, the stripes 24 may extend proximally from the distal end 14 of the annular wall 12. In some embodiments, a distal-most portion of each of the stripes 24 may be spaced apart from a distal-most surface of the distal end 14. In these embodiments, the stripes 24 may extend proximally from a position near the distal opening 20 but proximal to the distal opening within the distal end 14, which may increase a softness of a distal-most portion of the distal end 14, which may contact the vein wall of a patient. In these embodiments, the annular wall 12 may encapsulate or completely surround the stripes 24. In some embodiments, the stripes 24 may extend proximally from the distal opening 20 and/or the distal-most surface of the distal end 14. In some embodiments, the stripes 24 may be aligned or generally aligned with the longitudinal axis 22 of the tubular instrument 10.

Figure 2A:
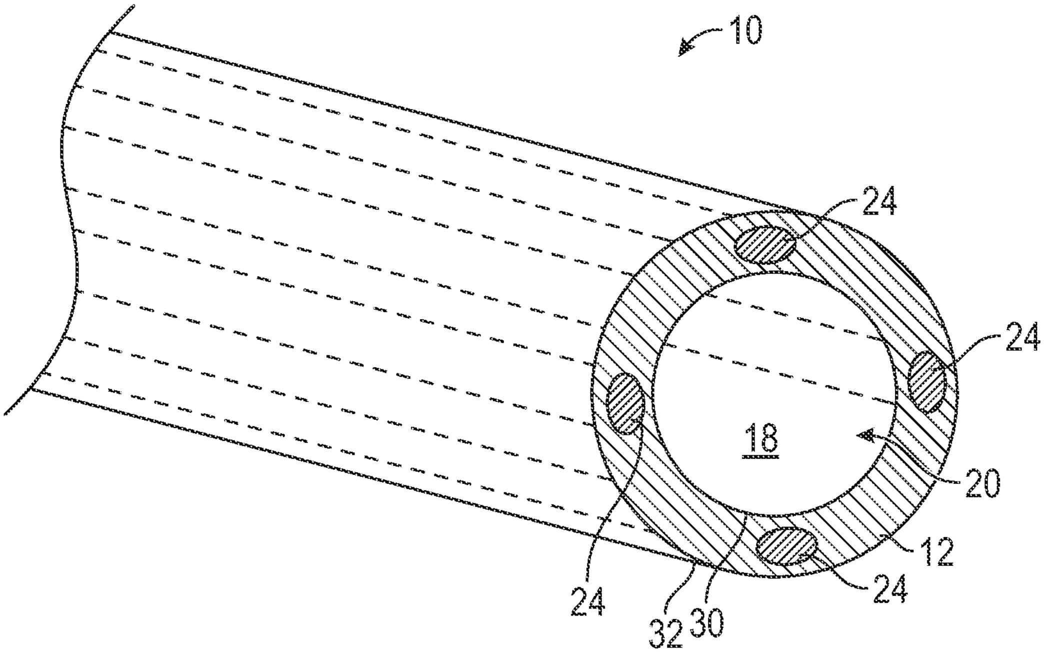
FIG. 2A is a transverse cross-sectional view of the tubular instrument of FIG. 1 along the line 2-2 of FIG. 1, according to some embodiments.

In some embodiments, a number of the stripes 24 may vary. In some embodiments, between one and three stripes 24 may be disposed within the annular wall 12. In some embodiments, more than three stripes 24 may be disposed within the annular wall 12. As illustrated in FIG. 2A, in some embodiments, the tubular instrument 10 may include four stripes 24. In some embodiments, the stripes 24 may be spaced around the annular wall 12. In some embodiments, the stripes 24 may be evenly spaced around the annular wall 12, as illustrated, for example, in FIG. 2A. In some embodiments, an outer perimeter of each of the stripes 24 may be surrounded by the annular wall 12 along all or a portion of its length, as illustrated, for example, in FIG. 2A.

In some embodiments, the stripes 24 may be co-extruded within the annular wall 12. In some embodiments, the stripes 24 may be constructed of a first material, and the annular wall 12 may be constructed of a second material. In some embodiments, the first material may have a greater durometer than the second material. Thus, in some embodiments, the stripes 24 may be stiffer than the annular wall 12.

In some embodiments, the first material may be thermoplastic. In some embodiments, the first material may include an elastomer, polyurethane, polyurethane, nylon, polyimide, silicon, or another suitable polymer. In some embodiments, the first material may include metal. In some embodiments, each of the stripes 24 may include a wire, which may be constructed of metal. In some embodiments, the wire may be configured to hold the tubular instrument 10 in a curved position in response to the wire being bent, which may position the tubular instrument 10 away from the vein wall or valve and into a center of the vein.

In some embodiments, the second material may be thermoplastic. In some embodiments, the second material may include polypropylene, polyurethane, polyurethane, nylon, polyimide, silicon, or another suitable polymer. In some embodiments, the second material may be similar to the first material but lower density.

In some embodiments, the stripes 24 may provide stiffness to the tubular instrument 10, which may facilitate advancement of the tubular instrument 10 through a catheter assembly and beyond the distal tip of the catheter without buckling. In some embodiments, the second material may be disposed on all or a portion of the outer surface and outer circumference of the tubular instrument 10, which may provide a softer contact surface with the vasculature.

In some embodiments, the annular wall 12 may include an inner surface 30 and an outer surface 32. In some embodiments, the inner surface 30 may be proximate the lumen 18 of the tubular instrument 10. In some embodiments, the inner surface 30 may be cylindrical and/or the stripes 24 may protrude to form ribs 34 on the outer surface 32. In some embodiments, other than the ribs 34 on the outer surface 32 formed by the stripes 24, the outer surface 32 may be cylindrical.

Figure 2B:
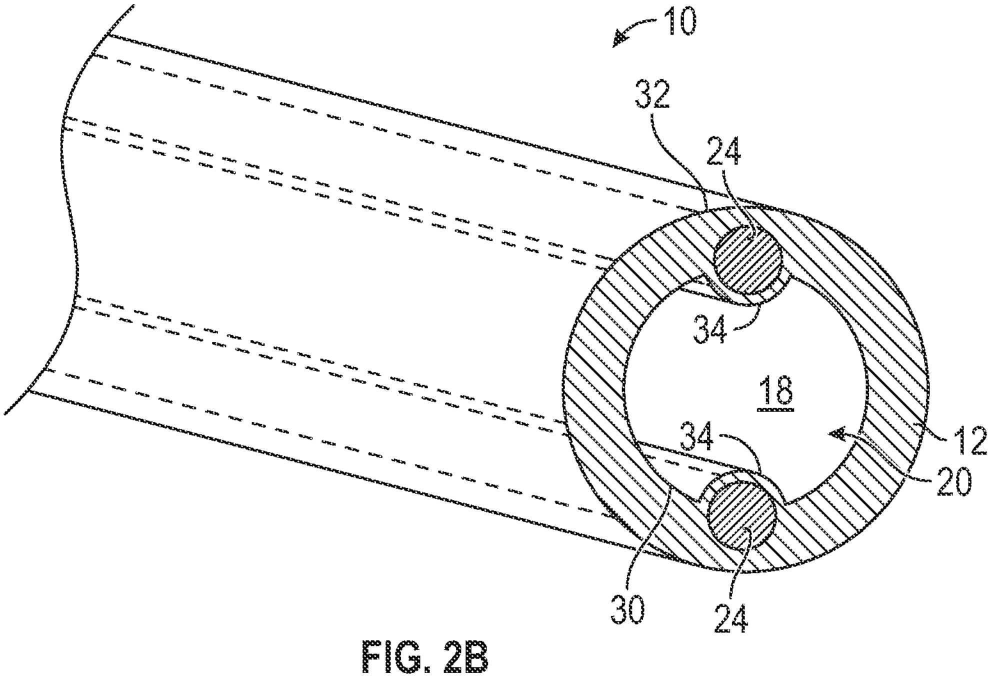
FIG. 2B is another transverse cross-sectional view of the tubular instrument of FIG. 1 along the line 2-2 of FIG. 1, according to some embodiments.
Figure 2C:
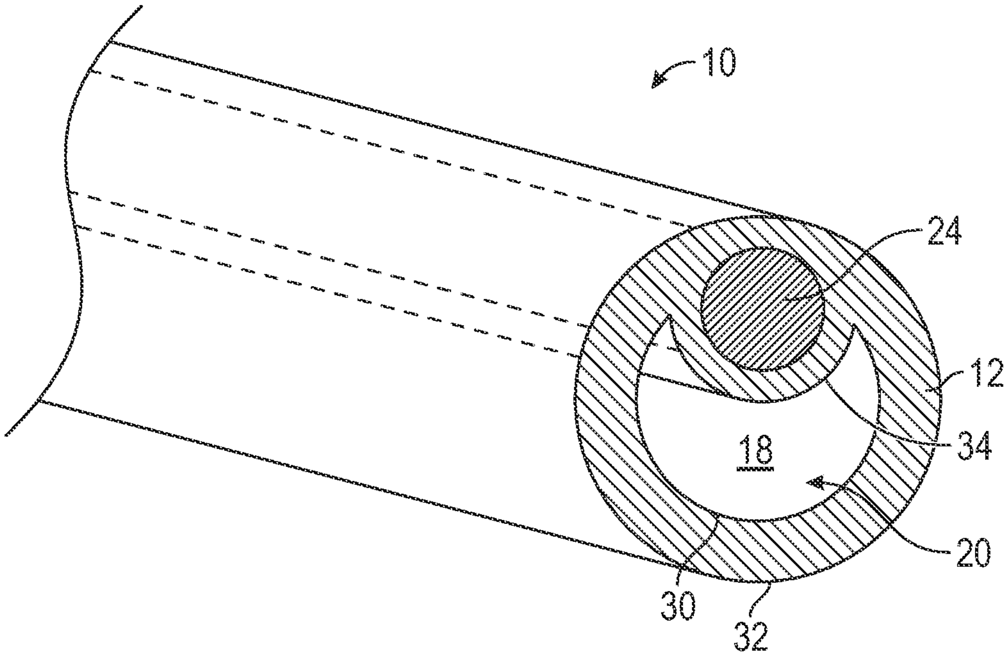
FIG. 2C is another transverse cross-sectional view of the tubular instrument of FIG. 1 along the line 2-2 of FIG. 1, according to some embodiments.
Figure 2D:
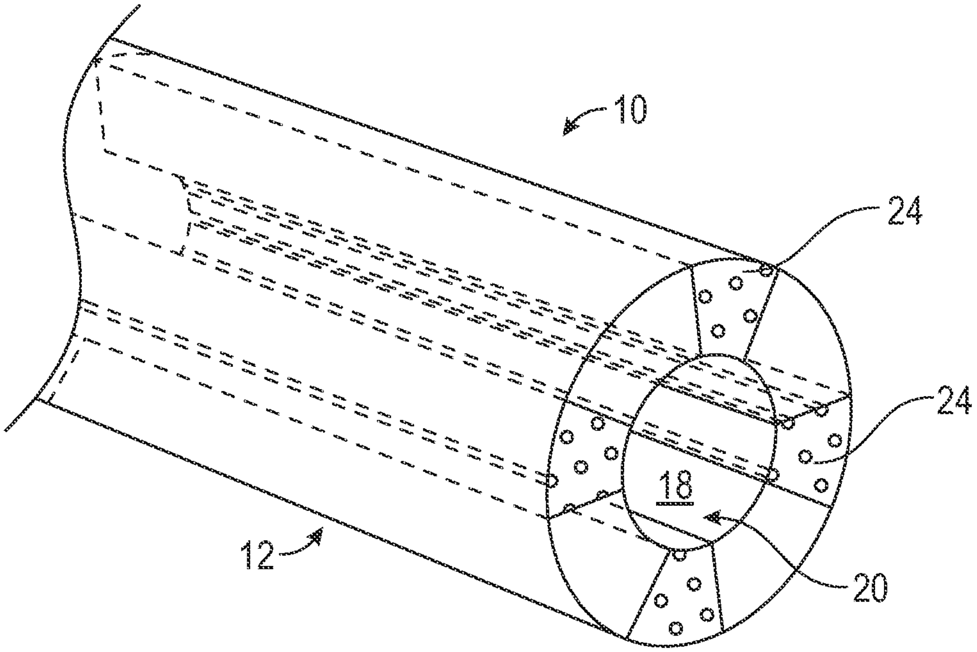
FIG. 2D is another transverse cross-sectional view of the tubular instrument of FIG. 1 along the line 2-2 of FIG. 1, according to some embodiments.

In some embodiments, the outer surface 32 may be cylindrical and/or the stripes 24 may protrude to form the ribs 34 on the inner surface 30, as illustrated, for example, in FIGS. 2B-2C. In some embodiments, other than the ribs 34 on the inner surface 30 formed by the stripes 24, the inner surface 30 may be cylindrical. In some embodiments, the tubular instrument 10 may include no more than one stripe 24, as illustrated, for example, in FIG. 2C. In some embodiments, the ribs 34 may reduce contact between the annular wall 12 and the vein wall. In some embodiments, the stripes 24 may extend through the annular wall 12, as illustrated, for example, in FIG. 2D.

Figure 2E:
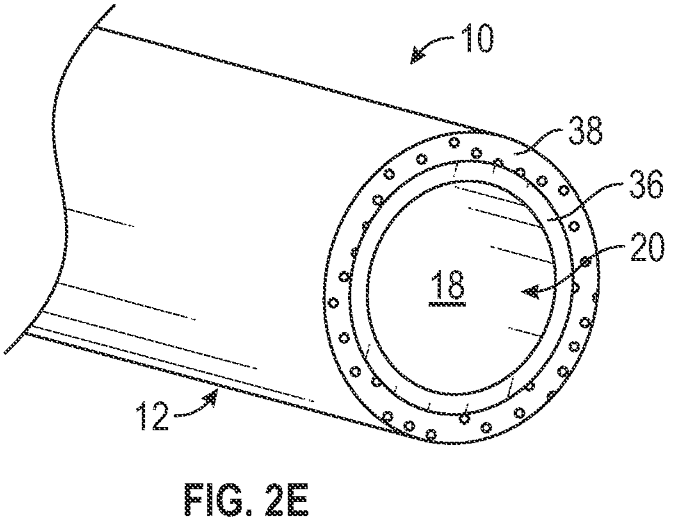
FIG. 2E is another transverse cross-sectional view of the tubular instrument of FIG. 1 along the line 2-2 of FIG. 1, according to some embodiments.

As illustrated, for example, in FIG. 2E, in some embodiments, the distal end 14 of the annular wall 12 may include a first annular layer 36 and a second annular layer 38. In some embodiments, the first annular layer 36 may be disposed within the second annular layer 38. In some embodiments, the second annular layer 38 may surround the first annular layer 36. In some embodiments, the first annular layer 36 may be constructed of the first material. In some embodiments, the second annular layer 38 may be constructed of the second material. In some embodiments, the first material may have a greater durometer than the second material.

In some embodiments, the first annular layer 36 and the second annular layer 38 may be concentrically co-extruded. In some embodiments, the first annular layer 36 may have a uniform or variable thickness along a length of the first annular layer 36. In some embodiments, the second annular layer 38 may have a uniform or variable thickness along a length of the second annular layer 38.

In some embodiments, the first annular layer 36 and/or the second annular layer 38 may extend along all or a portion of a length of the annular wall 12 between the distal end 14 and the proximal end 16. In some embodiments, the first annular layer 36 and/or the second annular layer 38 may extend proximally from the distal end 14 of the annular wall 12. In some embodiments, a distal-most portion of each of the first annular layer 36 may be spaced apart from a distal-most surface of the distal end 14. In these embodiments, the first annular layer 36 may extend proximally from a position near the distal opening 20 but proximal to the distal opening within the distal end 14, which may increase a softness of a distal-most portion of the distal end 14, which may contact the vein wall of a patient. In some embodiments, the first annular layer 36 and/or the second annular layer 38 may extend proximally from the distal opening 20 and/or the distal-most surface of the distal end 14.

Figure 2F:
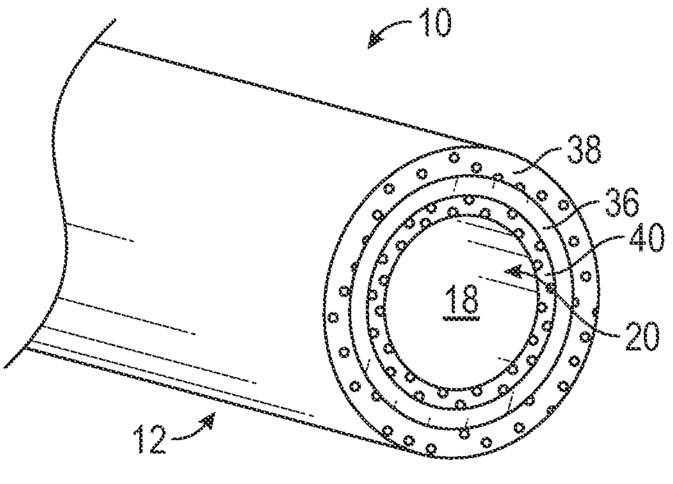
FIG. 2F is another transverse cross-sectional view of the tubular instrument of FIG. 1 along the line 2-2 of FIG. 1, according to some embodiments.

As illustrated, for example, in FIG. 2F, in some embodiments, the distal end 14 of the annular wall 12 may include a third annular layer 40, which may be disposed within the first annular layer 36 and the second annular layer 38. In some embodiments, the first annular layer 36 may surround and be proximate the third annular layer 40. In some embodiments, the third annular layer 40 may be constructed of the second material or a third material. In some embodiments, the first material may have a greater durometer than the third material. In some embodiments, the first annular layer 36, the second annular layer 38, and the third annular layer 40 may be concentrically co-extruded.

Referring now to FIGS. 3A-3D, the tubular instrument 10 is illustrated, according to some embodiments. In some embodiments, the first annular layer 36 and/or the second annular layer 38 may have a variable thickness along a length of the tubular instrument 10. In some embodiments, a stiffness of the tubular instrument 10 may progressively increase in a proximal direction. Thus, the distal end 14 may be stiffer than the proximal end 16, which may facilitate gentle, soft contact between the distal end 14 and the vein wall, while also preventing buckling.

Figure 3A:
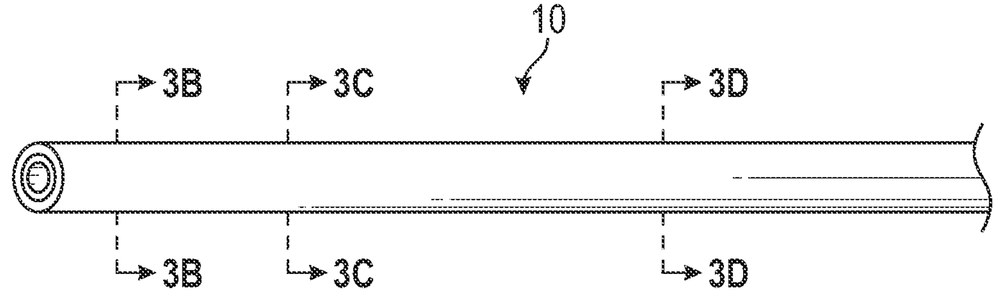
FIG. 3A is an upper perspective view of an example tubular instrument, according to some embodiments.
Figure 3B:
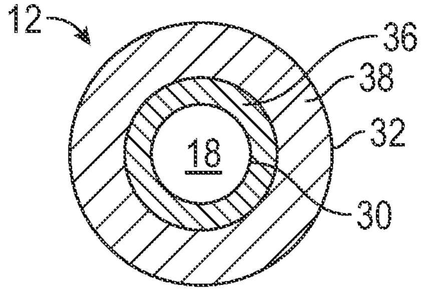
FIG. 3B is a transverse cross-sectional view of the tubular instrument of FIG. 3A along the line 3B-3B of FIG. 3A, according to some embodiments.
Figure 3C:
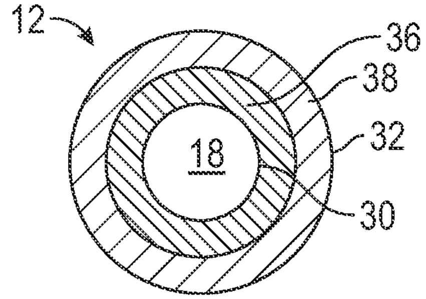
FIG. 3C is a transverse cross-sectional view of the tubular instrument of FIG. 3A along the line 3C-3C of FIG. 3A, according to some embodiments.
Figure 3D:
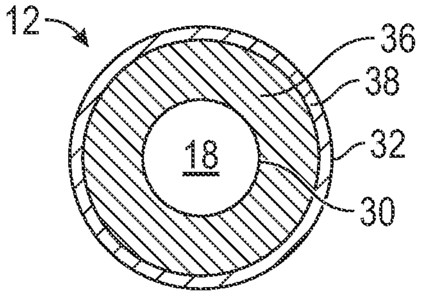
FIG. 3D is a transverse cross-sectional view of the tubular instrument of FIG. 3A along the line 3D-3D of FIG. 3A, according to some embodiments.

As illustrated, for example, in FIG. 3B, a thickness of the second annular layer 38 may be greater than a thickness of the first annular layer 36 at a first position along a length of the tubular instrument 10. As illustrated, for example, in FIG. 3C, the thickness of the second annular layer 38 may be a same thickness as the thickness of the first annular layer 36 at a second position along the length of the tubular instrument 10. In some embodiments, the second position may be proximal to the first position. As illustrated, for example, in FIG. 3D, the thickness of the second annular layer 38 may be less than the thickness of the first annular layer 36 at a third position along the length of the tubular instrument. In some embodiments, the third position may be proximal to the second position.

Figure 4A:
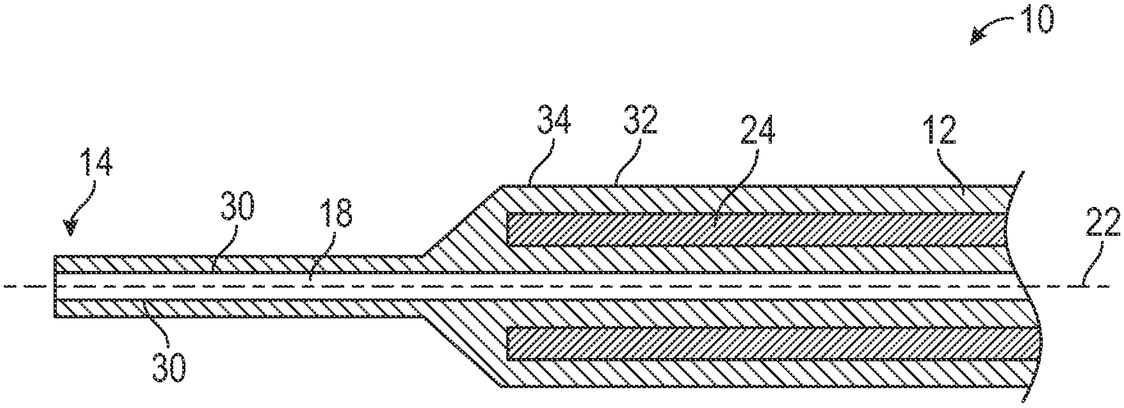
FIG. 4A is a longitudinal cross-sectional view of a portion of another example tubular instrument, according to some embodiments.
Figure 4B:
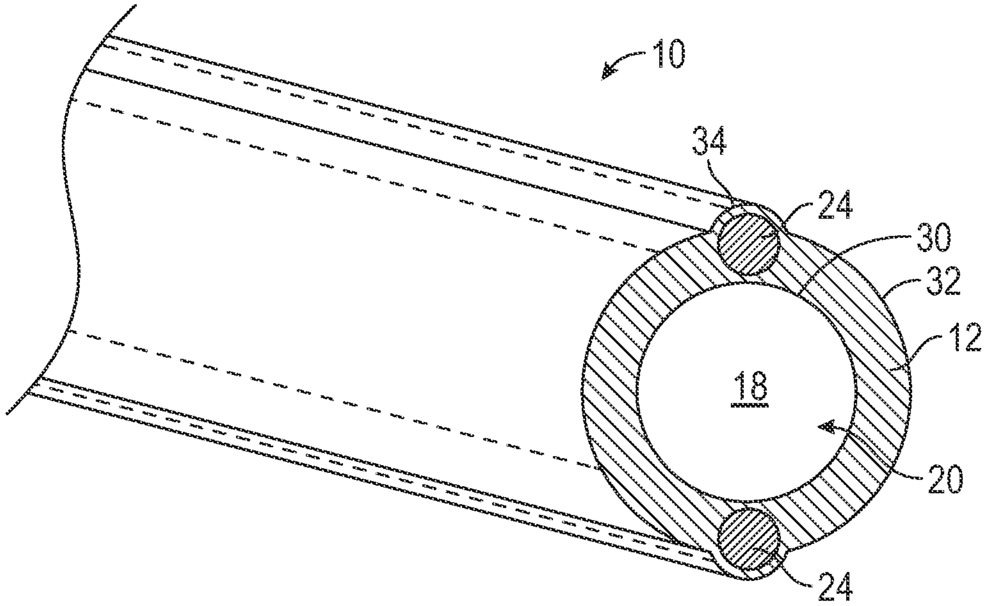
FIG. 4B is a transverse cross-sectional view of the tubular instrument of FIG. 4A, according to some embodiments.

Referring now to FIGS. 4A-4B, in some embodiments, a distal-most portion of each of the stripes 24 may be spaced apart from a distal-most surface of the distal end 14. In these and other embodiments, the inner surface 30 may be cylindrical and/or the stripes 24 may protrude to form ribs 34 on the outer surface 32. In some embodiments, other than the ribs 34 on the outer surface 32 formed by the stripes 24, the outer surface 32 may be cylindrical. In some embodiments, a portion of the tubular instrument 10 that includes the stripes 24 may have a greater outer diameter than a portion of the tubular instrument 10 without the stripes 24, such as a portion of the tubular instrument 10 proximate the distal-most surface of the distal end 14.

Figure 5A:
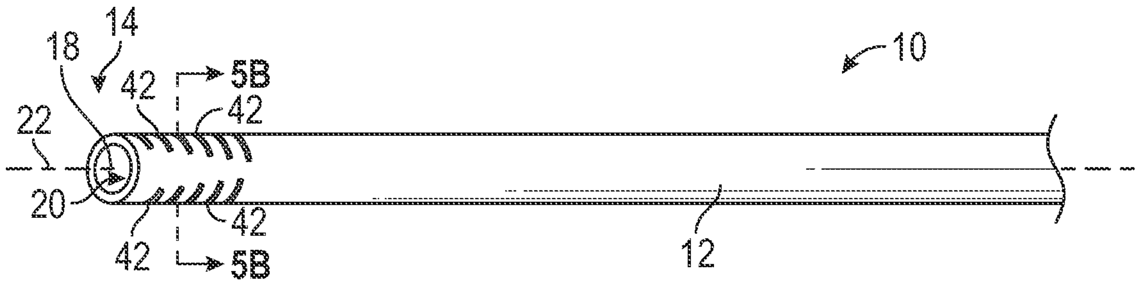
FIG. 5A is an upper perspective view of another tubular instrument, according to some embodiments.
Figure 5B:
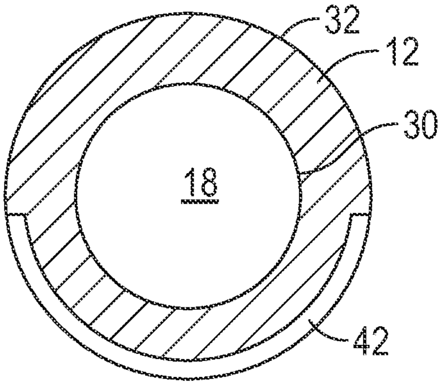
FIG. 5B is a transverse cross-sectional view of the tubular instrument of FIG. 5A along the line 5B-5B of FIG. 5A, according to some embodiments.

Referring now to FIGS. 5A-5B, in some embodiments, an outer surface of the distal end 14 of the tubular instrument 10 may include multiple grooves 42, which may improve a flexibility of the distal end 14. In some embodiments, the grooves 42 may include arc-shaped slots. In some embodiments, the grooves 42 may extend around a portion of an outer circumference of the distal end 14. In some embodiments, the tubular instrument 10 may be formed with a single or multiple material extrusion. In some embodiments, the tubular instrument 10 may be constructed of a single material, such as the first material, along an entire length of the tubular instrument 10 between the distal end 14 and the proximal end 16.

Figure 6:
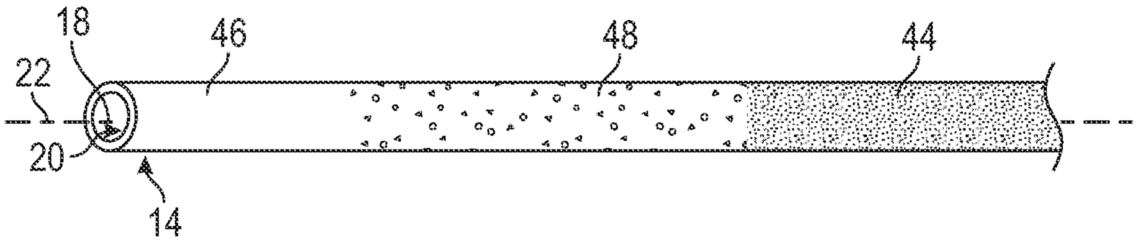
FIG. 6 is an upper perspective view of another example tubular instrument, according to some embodiments.

Referring now to FIG. 6, in some embodiments, the annular wall 12 may include a first annular section 44 and a second annular section 46 distal to the first annular section 44. In some embodiments, the first annular section 44 may be constructed of the first material. In some embodiments, the second annular section 46 may be constructed of the second material. In some embodiments, the durometer of the first material and the first annular section 34 may be greater than the durometer of the second material and the second annular section 46.

In some embodiments, the second annular section 46 may be disposed at a distal-most portion of the distal end 14, which may provide gentle, soft contact between the tubular instrument 10 and the vein wall. In some embodiments, the second annular section 46 may include the distal opening 20. In some embodiments, a thickness of the first annular section 44 may be greater than a thickness of the second annular section 46, which may provide an increased stiffness or durometer of the first annular section 44 compared to the second annular section 46.

In some embodiments, the first annular section 44 may include one or more of the stripes 24 (see, for example, FIGS. 2A-2D), which may be co-extruded within the first annular section 44. In some embodiments, the stripes 24 may be aligned with the longitudinal axis of the tubular instrument 10. In some embodiments, the stripes 24 may be constructed of the first material. In some embodiments, second annular section 46 and/or the annular wall 12 of the first annular section 44 may be constructed of the second material.

In some embodiments, the first annular section 44 may be proximate the second annular section 46 and there may be an abrupt change between the first annular section 44 and the second annular section 46, such as via bonding or another suitable method. In these embodiments, the first annular section 44 and the second annular section 46 may be joined together without a third annular section 48. In some embodiments, the first annular section 44 and the second annular section 46 may be a continuous structure or formed via a continuous extrusion.

In some embodiments, the annular wall 12 may include the third annular section 48 between the first annular section 44 and the second annular section 46. In some embodiments, the third annular section 48 may be proximate the first annular section 44 and the second annular section 46. In some embodiments, one or more of the first annular section 44, the second annular section 46, and the third annular section 48 may extend from an outer surface of the tubular instrument 10 inwardly to the lumen 18.

In some embodiments, the third annular section 48 may transition from the first annular section 44 to the second annular section 46. In some embodiments, the third annular section 48 may include a durometer in between the durometer of the first annular section 44 and the second annular section 46. In some embodiments, the third annular section 48 may include a joint that joins the first annular section 44 to the second annular section 46. In some embodiments, the joint may be formed via a solvent, adhesive bonding, swaging, ultrasound welding, tipping, or another suitable method.

Figure 7:
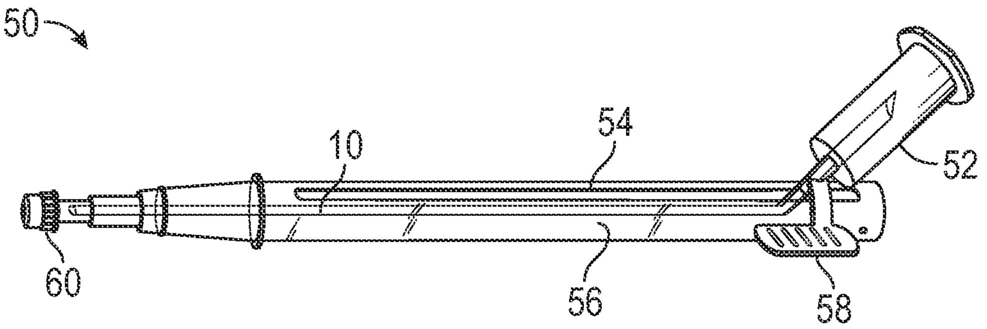
FIG. 7 is an upper perspective view of an example delivery device, according to some embodiments.

In some embodiments, the tubular instrument 10 may be coupled to any suitable delivery device. In some embodiments, the catheter of the catheter assembly may include one or more features of one or more of the tubular instruments 10 described with respect to FIGS. 1-6. FIGS. 7-9 illustrate several non-limiting examples of delivery devices. In some embodiments, the delivery device may be further described in U.S. patent application Ser. No. 16/037,246, filed Jul. 17, 2018, entitled "EXTENSION HOUSING A PROBE OR INTRAVENOUS CATHETER," U.S. patent application Ser. No. 16/388,650, filed Apr. 18, 2019, entitled "INSTRUMENT DELIVERY DEVICE HAVING A ROTARY ELEMENT," U.S. patent application Ser. No. 16/037,319, filed Jul. 17, 2018, entitled "MULTI-DIAMETER CATHETER AND RELATED DEVICES AND METHODS," U.S. patent application Ser. No. 16/502,541, filed Jul. 3, 2019, entitled "DELIVERY DEVICE FOR A VASCULAR ACCESS INSTRUMENT," U.S. patent application Ser. No. 16/691,217, filed Nov. 21, 2019, entitled "SYRINGE-BASED DELIVERY DEVICE FOR A VASCULAR ACCESS INSTRUMENT," U.S. patent application Ser. No. 16/742,013, filed Jan. 14, 2020, entitled "CATHETER DELIVERY DEVICE AND RELATED SYSTEMS AND METHODS," and U.S. patent application Ser. No. 16/838,831, filed Apr. 2, 2020, entitled "VASCULAR ACCESS INSTRUMENT HAVING A FLUID PERMEABLE STRUCTURE AND RELATED DEVICES AND METHODS," which are incorporated by reference in their entirety.

Figure 8A:
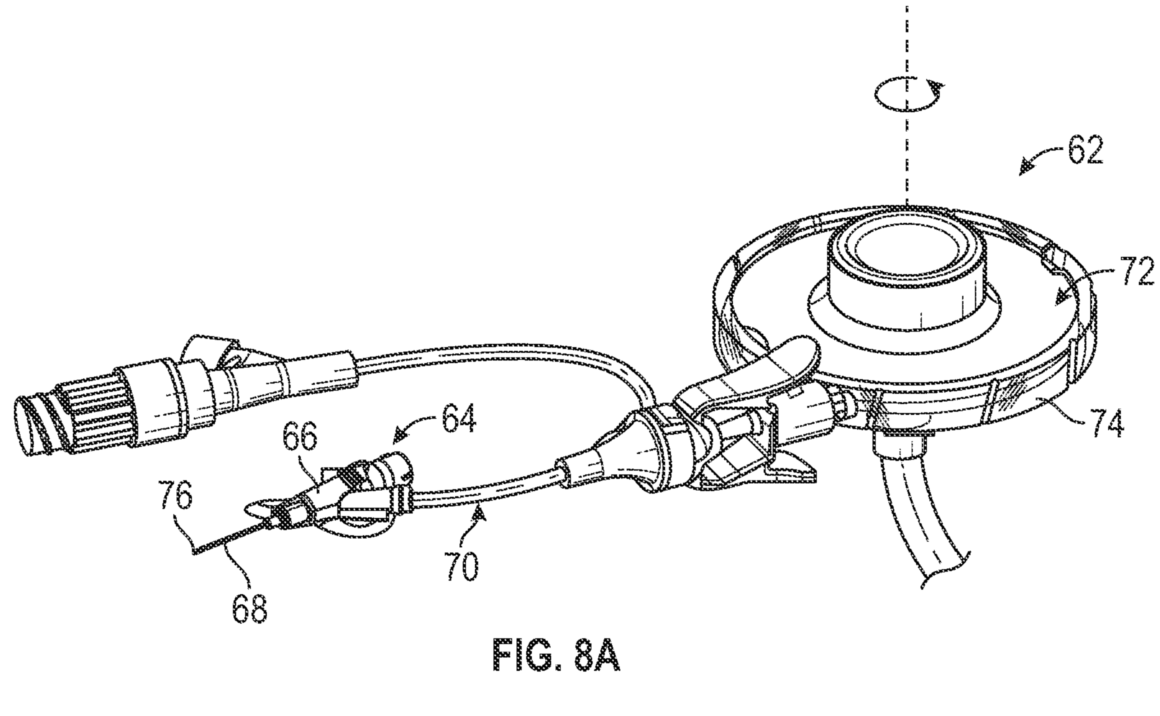
FIG. 8A is an upper perspective view of another example delivery device coupled to an example catheter assembly, according to some embodiments.
Figure 8B:
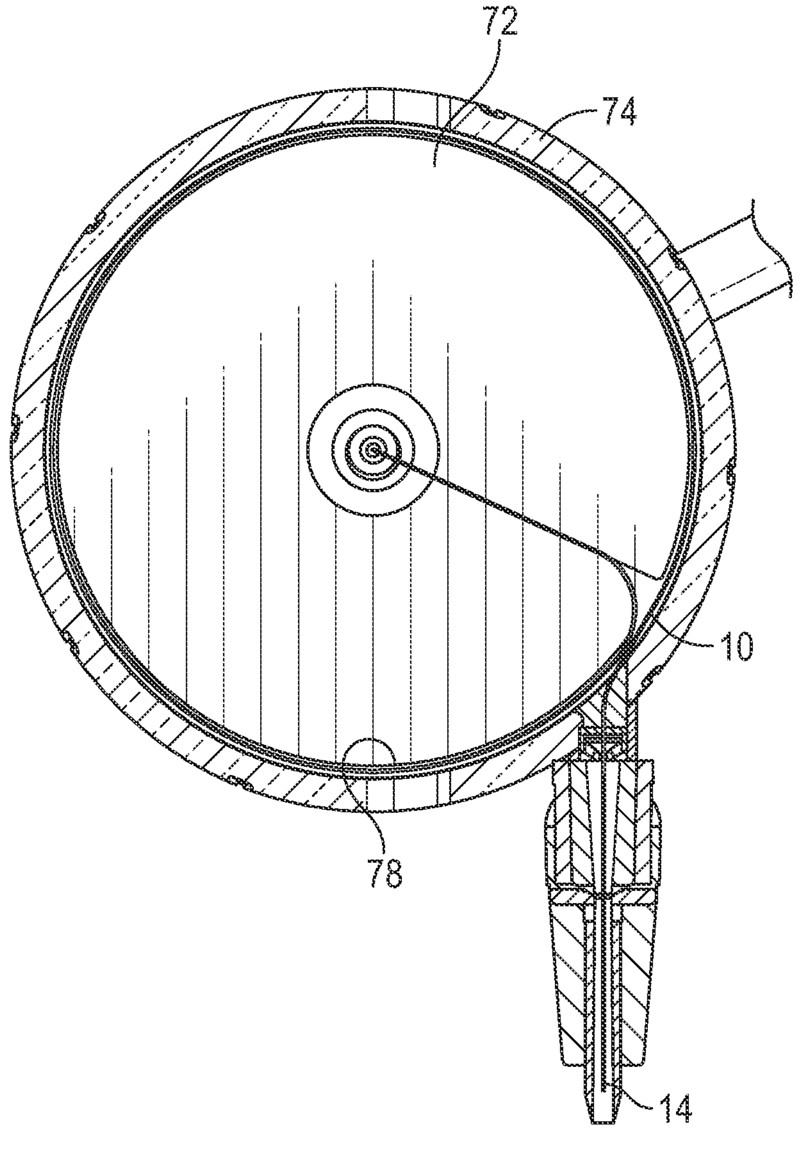
FIG. 8B is a cross-sectional view of the delivery device of FIG. 8A, according to some embodiments.
Figure 8C:
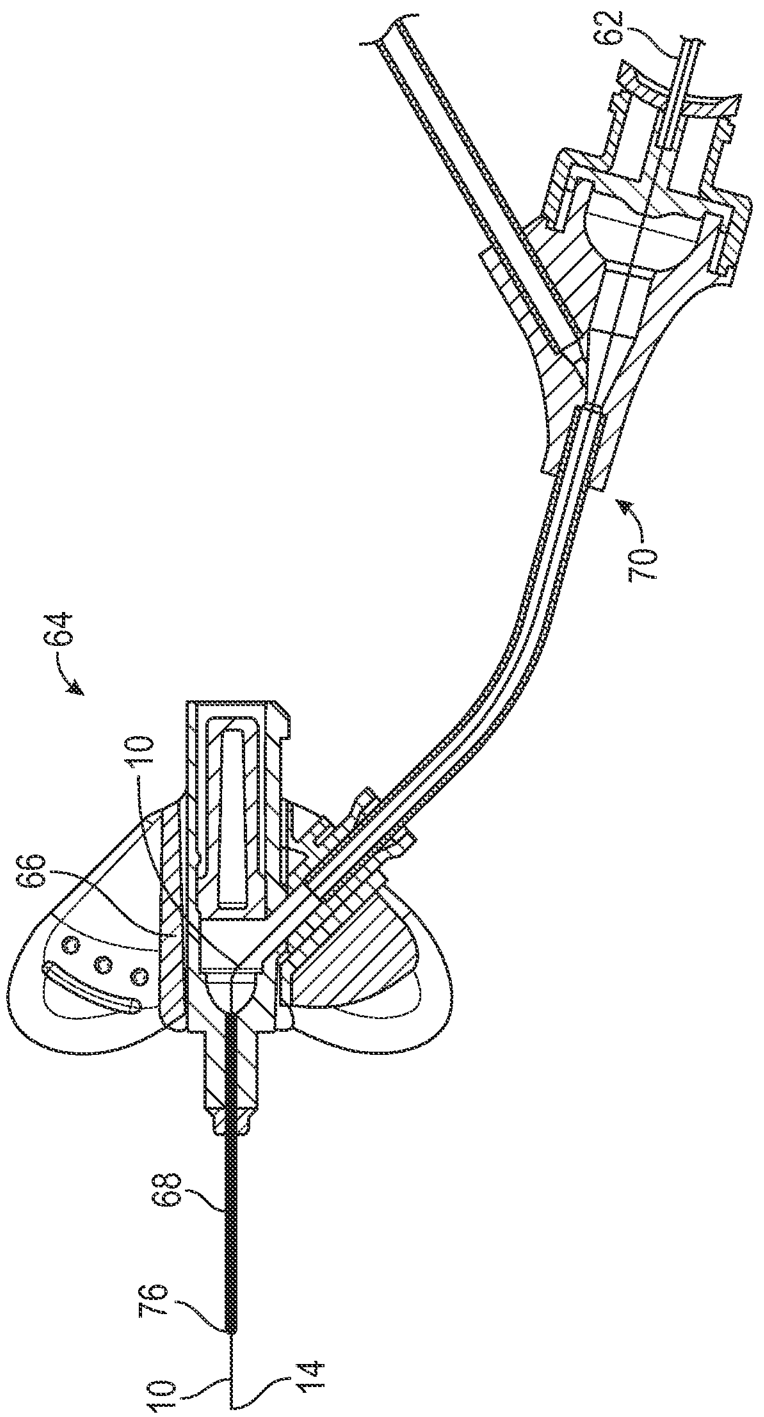
FIG. 8C a cross-sectional view of the catheter assembly of FIG. 8A, illustrating an example tubular instrument in an advanced or distal position, according to some embodiments.

Referring now to FIG. 7, in some embodiments, the delivery device 50 may deliver the tubular instrument 10 into a catheter of a catheter assembly, such as, for example, the catheter assembly 64 of FIGS. 8A and 8C. A catheter assembly 64 is illustrated in FIGS. 8A and 8C, according to some embodiments. In some embodiments, the delivery device 50 may include an extension, which may be proximate and/or coupled to a proximal end of a catheter adapter of the catheter assembly. In some embodiments, the extension may include an adapter 52, which may be coupled to the proximal end of the tubular instrument 10. In some embodiments, the adapter 52 may correspond to the Becton Dickinson VACUTAINER® one-use holder or a similar holder.

In some embodiments, the adapter 52 may be configured to move along a slot 54 in a housing 56 from a proximal position to a distal position and/or from the distal position to the proximal position. In some embodiments, in response to movement of the adapter 52 along the slot 54 from the proximal position to the distal position, the tubular instrument 10 may be advanced beyond the distal end of the housing 56. In some embodiments, in response to movement of the adapter 52 along the slot 54 from the distal position to the proximal position, the tubular instrument 10 may be withdrawn into the housing 56.

In some embodiments, the extension may include an advancement tab 58, which may be coupled to the proximal end of the tubular instrument 10 and/or the adapter 52. In some embodiments, the clinician may pinch or grasp the advancement tab 58 to move the tubular instrument 10 to the proximal position and/or the distal position. In some embodiments, the tubular instrument 10 may be advanced beyond the distal end of the housing 56 when the adapter 52 is disposed in the distal position. In some embodiments, the advancement tab 58 may be disposed in any number of locations.

In some embodiments, the distal end of the housing 56 may include a coupling mechanism 60, which may couple the delivery device 50 with the catheter assembly. In some embodiments, the coupling mechanism 60 may include a luer fitting.

Referring now to FIGS. 8A-8C, a delivery device 62 may be coupled to the catheter assembly 64. In some embodiments, the catheter assembly 64 may include the catheter adapter 66 and the catheter 68, which may extend distally from the catheter adapter 66. In some embodiments, the catheter 68 may be secured within the catheter adapter 66. In some embodiments, the catheter 68 may include a peripheral intravenous catheter ("PIVC"), peripherally inserted central catheter ("PICC") or a midline catheter.

In some embodiments, the delivery device 62 may be directly coupled to a proximal end of the catheter adapter 66. In these and other embodiments, the catheter assembly 64 may include a straight or non-integrated catheter assembly. In some embodiments, the delivery device 62 may be coupled to an extension set 70 of the catheter assembly 64 as illustrated in FIG. 8A. In these and other embodiments, the catheter assembly 64 may include an integrated catheter assembly. In further detail, in some embodiments, the catheter adapter 66 of the catheter assembly 64 may include an integrated extension tube, such as, for example, the BD NEXIVA™ Closed IV Catheter System, the BD NEXIVA™ DIFFUSICS™ Closed IV Catheter System, or the BD PEGASUS™ Safety Closed IV Catheter System.

In some embodiments, the delivery device 62 may include a rotary element 72 and a housing 74. In some embodiments, in response to rotation of the rotary element 72 with respect to the housing 74 in a first direction, the distal end 14 of the tubular instrument 10 may be advanced beyond a distal end 76 of the catheter 68. In some embodiments, in response to rotation of the rotary element 72 with respect to the housing 74 in the first direction, the distal end 14 of the tubular instrument 10 may be disposed at a first location with respect to the catheter assembly 64. An example first location is illustrated in FIG. 8B.

In some embodiments, in response to rotation of the rotary element 72 with respect to the housing 74 further in the first direction, the distal end 14 of the tubular instrument 10 may be disposed at a second location with respect to the catheter assembly 64. In some embodiments, the second location may be distal to the first location. An example second location is illustrated in FIG. 8C. In some embodiments, the tubular instrument 10 may be continuously advanced in the distal direction as the rotary element 72 is continuously turned.

In some embodiments, in response to rotation of the rotary element 72 with respect to the housing 74 in the first direction, the distal end 14 of the tubular instrument 10 may be disposed a first amount beyond the distal end 76 of the catheter 68. In some embodiments, in response to rotation of the rotary element 72 with respect to the housing 74 further in the first direction, the distal end 14 of the tubular instrument 10 may be disposed a second amount beyond the distal end 76 of the catheter 68. In some embodiments, the second amount may be greater than the first amount.

In some embodiments, the rotary element 72 may also rotate with respect to the housing 74 in a second direction opposite to the first direction. In some embodiments, in response to rotation of the rotary element 72 with respect to the housing 74 in the second direction, the distal end 14 of the tubular instrument 10 may be moved proximally.

In some embodiments, the rotary element 72 may include a support surface or groove 78, which may extend around at least a portion of a circumference of the rotary element 72. In some embodiments, the groove 78 may include a width approximately equal to or slightly greater than the tubular instrument 10, which may facilitate support of the tubular instrument 10.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A tubular instrument for fluid infusion or blood draw, deliverable into a catheter via a delivery device, the tubular instrument consisting of:

an annular wall comprising a distal end and forming a lumen, the lumen formed by the annular wall defining a fluid flow path;

a distal opening within the distal end of the annular wall; and a plurality of stripes within the annular wall, wherein the plurality of stripes are evenly spaced around the annular wall, wherein the plurality of stripes is co-extruded within the annular wall, wherein the plurality of stripes is constructed of a first material, wherein the annular wall is constructed entirely of a second material, and wherein the first material has a greater durometer than the second material, with the annular wall and the plurality of stripes forming an entirety of the tubular instrument;

wherein each of the plurality of stripes extends proximally within the annular wall from a position proximal to the distal opening, such that a distal-most portion of the annular wall does not include the plurality of stripes, and such that the distal-most portion of the annular wall has an increased softness as compared to a remaining proximally-positioned portion of the annular wall having the plurality of stripes therein; and wherein a portion of the distal end aligned with a longitudinal axis of the tubular instrument is closed, and wherein the distal opening is disposed laterally to the longitudinal axis and is formed through the annular wall.

2. The tubular instrument of claim 1, wherein each of the plurality of stripes is aligned with a longitudinal axis of the tubular instrument.

3. The tubular instrument of claim 1, wherein an outer perimeter of each of the plurality of stripes is surrounded by the annular wall.

4. The tubular instrument of claim 3, wherein the annular wall comprises an inner surface and an outer surface, and wherein each of the plurality of stripes protrudes to form a rib on the outer surface.

5. The tubular instrument of claim 3, wherein the annular wall comprises an inner surface and an outer surface, and wherein each of the plurality of stripes protrudes to form a rib on the inner surface.

6. The tubular instrument of claim 1, wherein each of the plurality of stripes extends proximally from the distal opening.

7. The tubular instrument of claim 1, wherein each of the plurality of stripes comprises a wire configured to hold the tubular instrument in a curved position.

8. The tubular instrument of claim 1, wherein the distal-most portion of the annular wall has a diameter that is smaller than a diameter of the remaining proximally-positioned portion of the annular wall having the plurality of stripes therein.

9. The tubular instrument of claim 1, wherein the distal end includes one or more diffusion holes that extend through the annular wall, the one or more diffusion holes formed through the annular wall at a location proximal to the distal opening and facilitating the fluid infusion or blood draw.

10. A system comprising:

a catheter assembly comprising a catheter adapter and a catheter extending distally from the catheter adapter;

a delivery device to deliver a tubular instrument into the catheter of the catheter assembly;

the tubular instrument, configured for fluid infusion or blood draw, the tubular instrument consisting of:

an annular wall comprising a distal end and forming a lumen, the lumen formed by the annular wall defining a fluid flow path;

a distal opening within the distal end of the annular wall; and a plurality of stripes within the annular wall, wherein the plurality of stripes is co-extruded within the annular wall, wherein the plurality of stripes is constructed of a first material, wherein the annular wall is constructed entirely of a second material, and wherein the first material has a greater durometer than the second material, with the annular wall and the plurality of stripes forming an entirety of the tubular instrument;

a housing, with the tubular instrument movable within the housing;

a coupling element positioned at a distal end of the housing and configured to secure the delivery device to the catheter assembly; and an advancement mechanism configured to move the tubular instrument relative to the housing and relative to the catheter, with the tubular instrument movable from a first location with respect to the coupling element to a second location with respect to the coupling element, and with the tubular instrument extending out distally from the coupling element and into or through the catheter when at the second location;

wherein each of the plurality of stripes extends proximally within the annular wall from a position proximal to the distal opening, such that a distal-most portion of the annular wall does not include the plurality of stripes, and such that the distal-most portion of the annular wall has an increased softness as compared to a remaining proximally-positioned portion of the annular wall having the plurality of stripes therein; and wherein the annular wall has an outer diameter that is less than an inner diameter of a catheter lumen of the catheter, to enable delivery of the tubular instrument into and through the catheter.

11. The system of claim 10, wherein the delivery device further comprises an adapter coupled to the proximal end of the tubular instrument.

12. The system of claim 11, wherein the adapter comprises a device for the collection of blood specimens.

13. The system of claim 11, wherein the advancement mechanism comprises an advancement tab coupled to the proximal end of the tubular instrument and/or to the adapter, the advancement tab movable relative to the housing to move the tubular instrument from the first location to the second location.

14. The system of claim 10, wherein the distal-most portion of the annular wall has a diameter that is smaller than a diameter of the remaining proximally-positioned portion of the annular wall having the plurality of stripes therein.

* * * * *